United States Patent
Galjour

[11] Patent Number: 5,947,942
[45] Date of Patent: Sep. 7, 1999

[54] COLOSTOMY BAG BELT

[76] Inventor: David M. Galjour, 3408 Arizona St., Kenner, La. 70065

[21] Appl. No.: 08/896,876

[22] Filed: Jul. 18, 1997

[51] Int. Cl.⁶ .......................................................... A61F 5/44
[52] U.S. Cl. ............................................................. 604/345
[58] Field of Search ..................................... 604/332–345

[56] References Cited

U.S. PATENT DOCUMENTS

| | | | |
|---|---|---|---|
| 2,612,895 | 10/1952 | Magee . | |
| 2,656,838 | 10/1953 | McConnell | 604/345 |
| 3,398,744 | 8/1968 | Hooper | 604/345 |
| 3,481,336 | 12/1969 | Ipson | 604/345 |
| 4,256,110 | 3/1981 | Scoville | 604/332 |
| 4,738,661 | 4/1988 | Marut . | |
| 5,135,520 | 8/1992 | Beaupied . | |
| 5,234,420 | 8/1993 | Horton et al. . | |
| 5,653,701 | 8/1997 | Millman | 604/345 |

Primary Examiner—John G. Weiss
Assistant Examiner—Dennis Ruhl
Attorney, Agent, or Firm—Joseph N. Breaux

[57] ABSTRACT

A colostomy bag belt which utilizes: an inner comfort belt which holds a skin patch against the wearer's skin, the skin patch being connected to a connector forming a conduit through the comfort belt; an exterior belt which forms a pouch therein and has a leak-proof safety pouch within the belt and has a connector forming a conduit through the exterior belt and into the safety pouch and which has a sealable opening through which as colostomy bag can be inserted into the safety pouch and secured to the connector; a flexible intermediate connector which completes the conduit from the skin patch to the safety pouch; and a colostomy bag placed in the safety pouch and connected to the conduit to receive the waste which exits the stoma and passes through the conduit.

17 Claims, 3 Drawing Sheets ic 5,947,942

COLOSTOMY BAG BELT

TECHNICAL FIELD

The present invention relates to medical devices and more particularly to medical devices for supporting colostomy bags that utilize an inner comfort belt and an exterior belt, the comfort belt holding a skin patch against the wearer's skin, the exterior belt forming a pouch and having a leak-proof safety pouch therein, the skin patch being connected to a colostomy bag through a connector in the comfort belt, an expandable intermediate connector and a connector in the exterior belt.

BACKGROUND OF THE INVENTION

Following the surgical removal of the colon (a "colostomy"), patients require means for removing bodily waste from their intestinal tracts. Typically, this is accomplished by routing the waste through a stoma which exits the body. The waste then empties into a colostomy bag secured at the external end of the stoma.

The arrangement described above can be uncomfortable and unattractive and can create an unpleasant smell. Existing means for supporting a colostomy bag are somewhat fragile and must be handled with care in order to avoid detaching the colostomy bag and damaging the stoma. These existing means are prone to leakage and may prevent the wearer from participating in activities which could jar or damage the colostomy bag or support. The invention provides a means for preventing leakage and odor from the colostomy bag and also prevents damage to the stoma.

SUMMARY OF THE INVENTION

It is thus an object of the invention to provide a colostomy bag belt that provides a secure attachment of the bag to the wearer.

It is a further object of the invention to provide a colostomy bag belt that prevents odor from escaping from a colostomy bag.

It is a still further object of the invention to provide a colostomy bag belt that prevents a colostomy bag from being accidentally detached.

It is a still further object of the invention to provide a colostomy bag belt that contains within a safety enclosure any spillage from a colostomy bag which leaks, breaks or becomes detached.

It is a still further object of the invention to provide a colostomy bag belt that utilizes a first belt to secure the skin patch against the wearer's skin and a second belt which is connected to the first belt by means of a flexible conduit and supports a colostomy bag in a leak-proof safety pouch.

Accordingly, a colostomy bag belt meeting the above objects is provided. The invention utilizes an inner comfort belt which holds a skin patch against the wearer's skin, the skin patch being connected to a connector forming a conduit through the comfort belt. The invention further utilizes an exterior belt which forms a pouch therein and has a leak-proof safety pouch within the belt and has a connector forming a conduit through the exterior belt and into the safety pouch. The connectors of the comfort and exterior belts are connected by a flexible intermediate connector so that there is a conduit from the skin patch to the safety pouch, a colostomy bag being placed in the safety pouch and connected to the conduit to receive the waste which exits the stoma and passes through the conduit.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

DESCRIPTION OF THE EXEMPLARY EMBODIMENT

Figure 1:
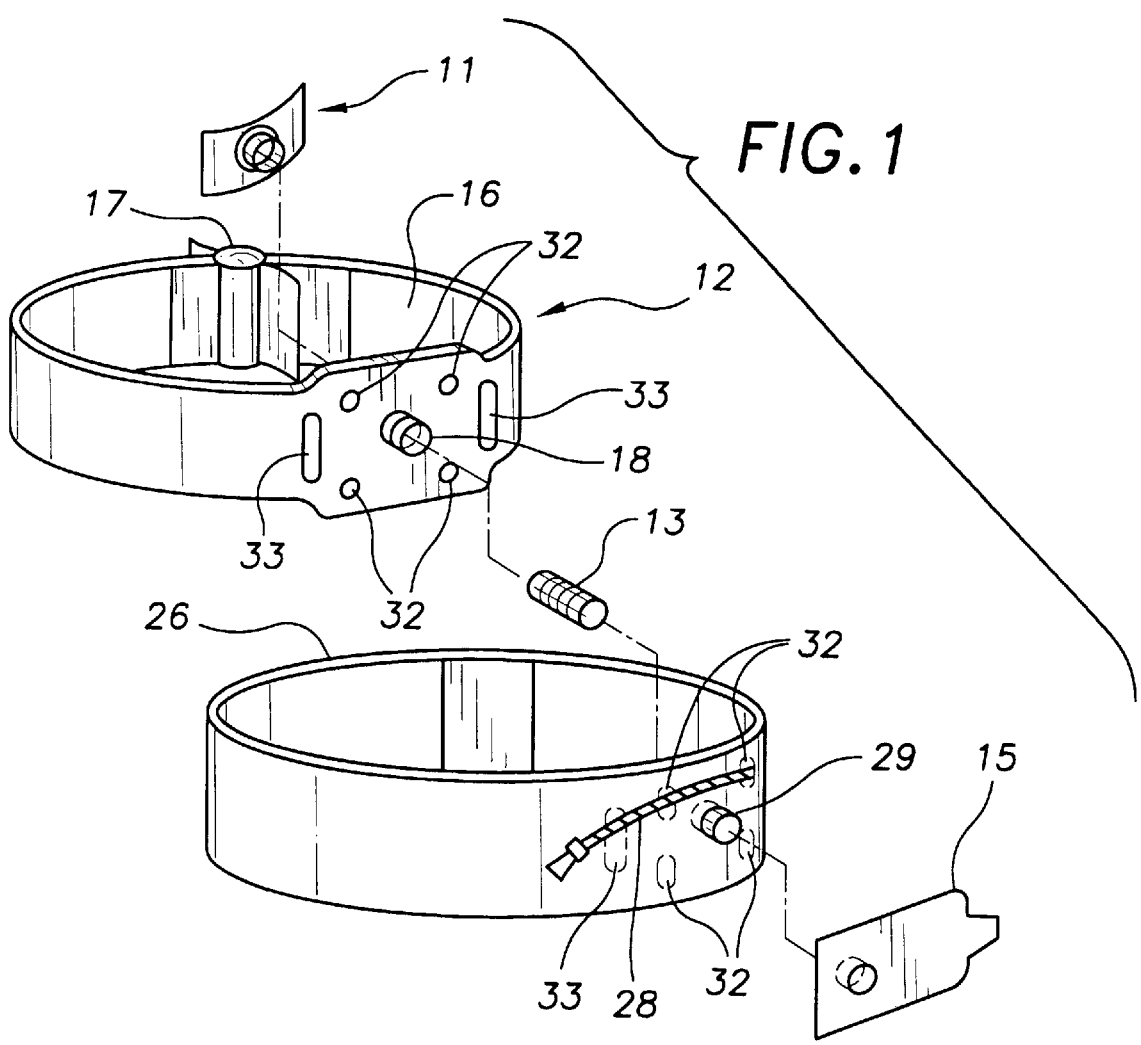
FIG. 1 is an exploded perspective view of the preferred embodiment of the invention.
Figure 2:
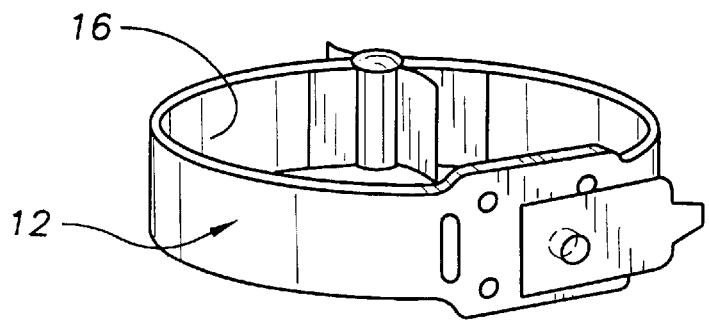
FIG. 2 is a perspective view of an alternate embodiment of the invention which does not require the exterior belt.
Figure 3:
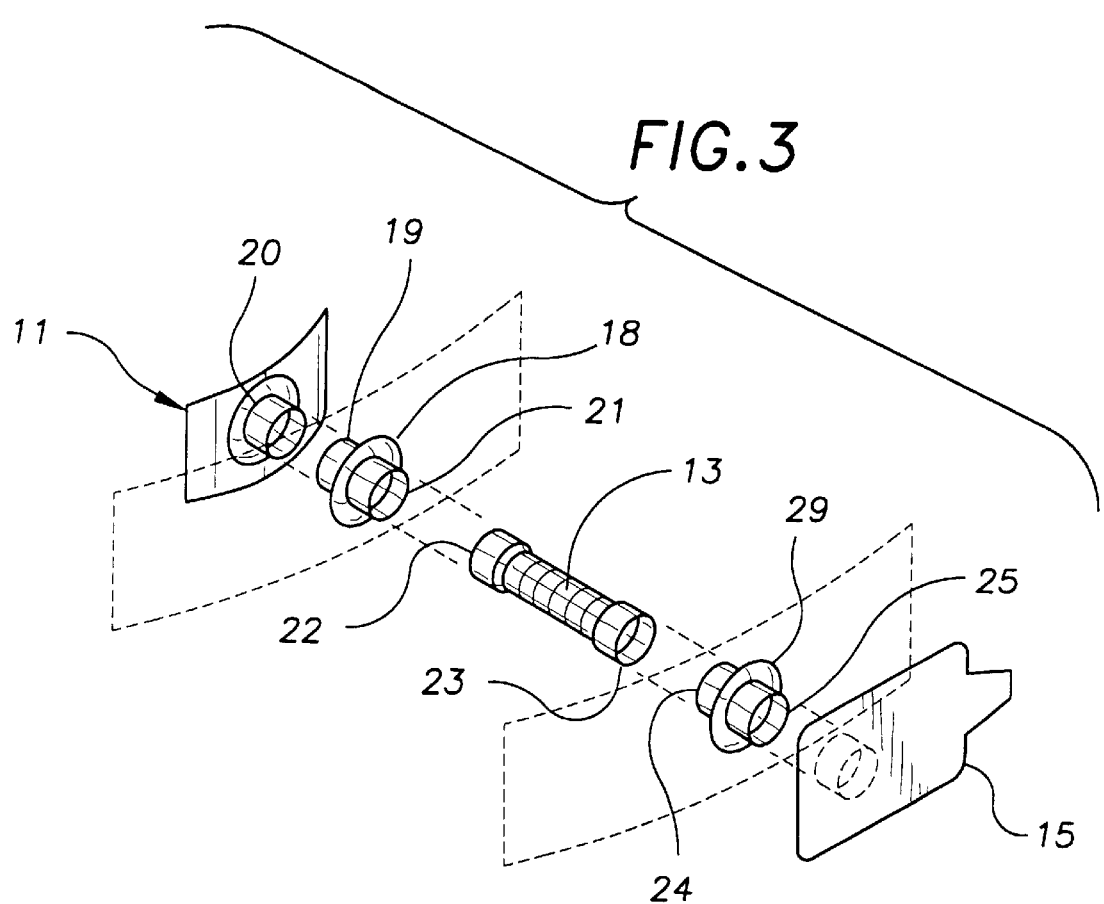
FIG. 3 is an exploded perspective view of the connectors forming the conduit of the preferred embodiment of the invention.

Referring to FIG. 1, an exploded perspective view of the preferred embodiment of the invention, generally designated by the numeral 10, is shown. The invention comprises a skin patch connector 11, a comfort belt generally designated by the numeral 12, a intermediate connector 13, an exterior belt generally designated by the numeral 14 and a colostomy bag 15.

Comfort belt 12 is worn next to the wearer's skin and is also called the comfort belt. The comfort belt is manufactured from cloth or some other breathable material. A removable pad 16 is attached to the inner surface of the comfort belt 12. Removable pad 16 is disposable and is constructed of a multi-layer, absorbent material so that the layer which is in contact with the wearer's skin and which thereby becomes soiled can simply be peeled from the pad and thrown away.

The comfort belt 12 has a hook-and-loop closure 17 in which the hook material is sewn onto one end of the belt and the loop material is sewn onto the other end of the belt so that the ends of the belt can be adjustably closed around the waist of the wearer. The comfort belt has an aperture midway between the ends through which the stoma can be inserted. A comfort belt connector 18 is installed in the aperture. Comfort belt connector 18 has an inwardly facing mating surface 19 which is female and which is connected to the male mating surface 20 of skin patch connector 11. Comfort belt connector 18 also has an outwardly facing male mating surface 21 which is connected to intermediate connector 13 via female mating surface 22.

Skin patch connector 11 has a wide inner surface 35, sometimes called a skin patch, which fits against the wearer's skin. When fastened around the wearer's waist, the comfort belt 12 holds the skin patch connector 11 in place against the wearer's skin.

Exterior belt 14 has an outer fabric portion 26 which contains an interior safety pouch 27. Outer fabric portion 26 has a plastic buckle 36 to fasten the belt around the wearer's waist. Hook and loop materials are also sewn into the ends of the outer fabric portion in the same manner as comfort belt 12 to secure the ends of the belt. A pocket for holding extra colostomy bags may be attached to the outer surface of the outer fabric portion of the belt.

The outer fabric portion 26 forms a pouch within which interior safety pouch 27 is disposed. Connector 29 forms an aperture through the inwardly facing walls of interior safety pouch 27 and outer fabric portion 26 to provide access to the safety pouch.

Figure 4:
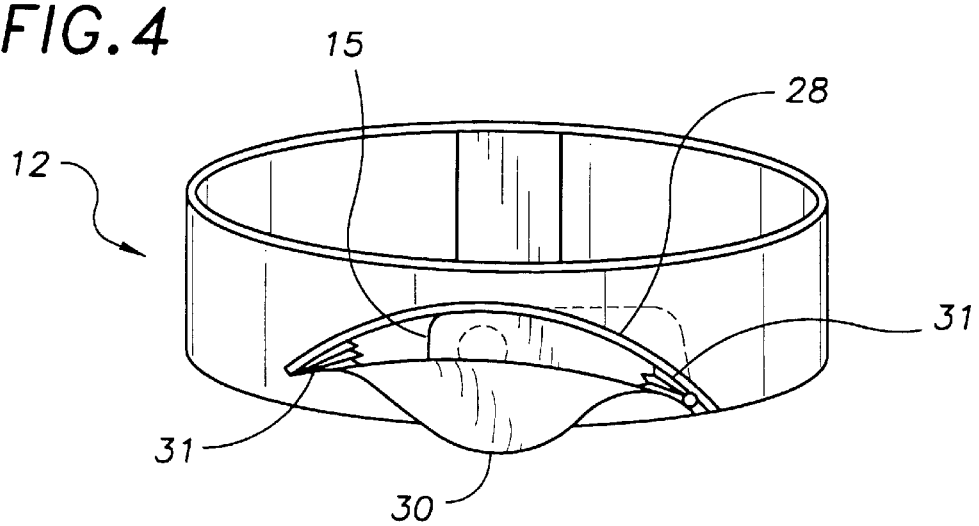
FIG. 4 is a front view of the exterior belt of the preferred embodiment with the flap opening extended forward.
Figure 5:
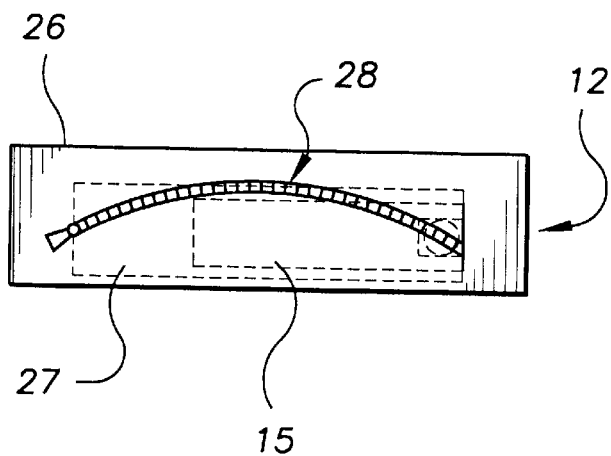
FIG. 5 is a front plan view of the preferred embodiment of the invention.
Figure 6:
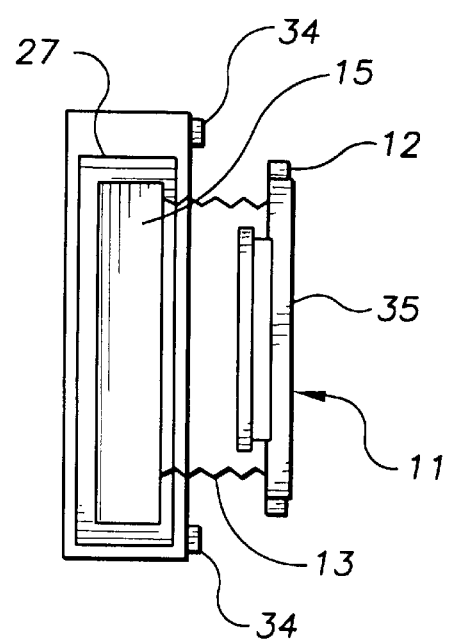
FIG. 6 is a front plan view of the preferred embodiment of the invention.

Referring to FIG. 4, the outwardly facing surfaces of interior safety pouch 27 and outer fabric portion 26 have an opening which is closeable by means of a zipper 28 which seals the edges of the opening. The zipper is a plastic type zipper which forms a fluid-tight seal to prevent fluids and odors from escaping the interior safety pouch. Zipper 28 forms an upwardly arched curve so that, when the opening is unzipped, a flap 30 is formed in the outwardly facing surfaces of the interior safety pouch 27 and outer fabric portion 26. At the sides of flap 30 are pleats 31 which allow the flap to be extended outward while maintaining a reservoir to contain any fluids within the safety pouch 27 rather than allowing these fluids to escape from the interior of the pouch. "Pleats" here refers not simply to the folds in the sidewall material, but to the sidewalls themselves.

As described above, connector 29 extends to the interior of safety pouch 27. A colostomy bag 15 is placed within interior safety pouch 27, where the colostomy bag is attached to connector 29. Anything entering exterior belt 14 through connector 29 is thus contained within colostomy bag 15. In the event that there is leakage from colostomy bag 14 or the connection between the bag and connector 29, the leakage is contained within interior safety pouch 27. Rubber grips 34 around the edge of inner surface 35 hold it in place and provide improved sealing between the surface and the skin.

Comfort belt 12 and exterior belt 14 are connected by attaching intermediate connector 13 to connector 29 with female mating surface 23 adjoining inwardly facing male mating surface 24. A conduit is thereby formed from the stoma to the colostomy bag, the conduit beginning at skin patch connector 11 and extending through comfort belt connector 18, intermediate connector 13 and connector 29.

Intermediate connector 13 has accordion-style ribs which allow the connector to flex and expand so that the connection between the comfort and exterior belts can tolerate movement without losing its integrity. In addition to being connected by intermediate connector 13, the comfort and exterior belts are connected by several sets of matings snaps 32 and mating hook and loop material patches 33. These sets of snaps and hook-and-loop patches are located around connectors 13, 18 and 29. The snaps 32 serve to align the comfort and exterior belts. The hook-and-loop patches 33 do not assist in the alignment of the comfort and exterior belts, but do provide additional strength which the snaps do not have and thereby prevents the comfort and exterior belts from being pulled apart.

Connectors 11, 13, 18 and 29 are made of nylon and are formed using an injection molding process. Interior safety pouch 27 is manufactured from heavy gauge vinyl. The sides of the pouch are cut from sheets of vinyl and the edges of these sheets are bonded together using heat welding to provide a leak-proof seam. Leak-proof zipper 28 is also made of vinyl and is heat welded to the edges of the safety pouch.

Exterior belt 14 is made of a durable fabric such as woven nylon or a rubberized laminate cloth. The exterior belt is sewn together in the same manner as any other garment and conventional stitching techniques are used to strengthen the exterior belt in the appropriate areas.

The invention provides several advantages to persons having to wear colostomy bags. The safety pouch provides an extra level of protection against odor escaping from the colostomy bag. If a colostomy bag breaks, the contents of the bag will be contained within the safety pouch, thereby preventing spillage and associated odors. The containment of the colostomy bag within the exterior belt prevents the accidental pulling or dislodging of the bag. If, however, the bag is accidentally pulled, the hook-and-loop patches and the snaps connecting the comfort and exterior belts will absorb some of the stress and the expandable intermediate connector allows the bag to be extended away from the comfort belt before becoming disconnected. The intermediate connector also helps to confine any spillage to the safety pouch in the event that the colostomy bag is disconnected.

The invention is utilized by placing the comfort belt at the wearer's waist and placing the stoma through the skin patch connector 11 and comfort belt connector 18. The comfort belt is then adjusted so that it is firmly but comfortably secured around the wearer's waist. Then, one end of the flexible intermediate connector 13 is attached to the comfort belt connector 18 and the other end of the intermediate connector 13 is attached to the exterior belt connector 29. Snaps 32 are then connected to ensure the belts are properly aligned and hook-and-loop patches 33 are connected to secure the belts together. After the snaps and hook-and-loop patches are connected, the exterior belt is placed around the wearer's waist, adjusted for proper fit and secured using the buckle and hook-and-loop closure. When the comfort and exterior belts are securely in place, the stoma is checked to be sure it is in place through the connectors. The colostomy bag is then attached to the exterior belt connector and the bag is placed within the safety pouch. The colostomy bag can be placed in the safety pouch so that the bag extends either to the right side of the connectors as necessary for the comfort of the wearer.

In addition to the above usage, the comfort belt can be used alone with a colostomy bag attached to comfort belt connector 18. The comfort belt provides a means for securing the colostomy bag for collection of the waste exiting the body through the stoma.

It can be seen from the preceding description that a method and device for supporting a colostomy bag which provides a secure attachment of the bag to the wearer, prevents odor from escaping from the colostomy bag, prevents the colostomy bag from being accidentally detached and contains within a safety enclosure any spillage from a colostomy bag which leaks, breaks or becomes detached and which utilizes a first belt to secure the skin patch against the wearer's skin and a second belt which is connected to the first belt by means of a flexible conduit and supports a colostomy bag in a leak-proof safety pouch has been provided.

It is noted that the embodiment of the colostomy bag belt described herein in detail for exemplary purposes is of course subject to many different variations in structure, design, application and methodology. Because many varying and different embodiments may be made within the scope of the inventive concept(s) herein taught, and because many modifications may be made in the embodiment herein described in accordance with the descriptive requirements of the law, it is to be understood that the details herein are to be interpreted as illustrative and not in a limiting sense.

What is claimed is:

1. A colostomy bag belt comprising:

a skin patch connector having a skin-facing surface, a mating surface and a first aperture extending through said skin patch connector from said skin-facing surface to said mating surface;

a comfort belt having a first inner surface, a first outer surface and a first adjustable closure, said comfort belt having a second aperture therethrough and a tubular inner belt connector disposed in said second aperture, said comfort belt further having a removable multi-layer pad attached to said first inner layer;

an exterior belt having a second inner surface, a second outer surface and a second adjustable closure, said exterior belt having a first pouch formed integrally therein, said exterior belt having a second, leak-proof pouch disposed within said first pouch, said second, leak-proof pouch having a first wall adjoining said second inner surface and a second wall adjoining said second outer surface, said exterior belt having a tubular exterior belt connector disposed within a third aperture which extends through said second inner surface and said first wall, said exterior belt further having a curved opening through said second outer surface and said second wall which allows access to the interior of said second, leak-proof pouch, said curved opening being closeable by a leak-proof zipper which extends along the edges of said curved opening, said curved opening forming a flap which is outwardly extendable from said curved opening, said exterior belt further having two pleats, one of each of said pleats being disposed on each end of said curved opening to form a reservoir when said flap is outwardly extended;

said skin patch connector being connected in mating fashion to said inner belt connector;

an expandable intermediate connector having a first end and a second end, said first end being connected in mating fashion to said inner belt connector, said second end being connected in mating fashion to said exterior belt connector, said expandable intermediate connector having accordion-style folds which allow said first and second ends to move with respect to each other while maintaining said mating connections;

a plurality of mating pairs of snaps, each pair having a male snap and a female snap, one snap of each of said pairs of snaps being attached to said first outer surface of said comfort belt around said comfort belt connector, the other snap of each of said pairs of snaps being attached to said second inner surface of said exterior belt around said exterior belt connector and in alignment with said snaps attached to said comfort belt;

a plurality of pairs of mating hook-and-loop patches, each pair having a patch of hook material and a patch of loop material, one patch of each pair being attached to said first outer surface of said comfort belt around said comfort belt connector, the other patch of each of said pairs of patches being attached to said second inner surface of said exterior belt around said exterior belt connector and in alignment with said patches attached to said comfort belt;

a colostomy bag attached to said exterior belt connector, a conduit being formed through said skin patch connector, said inner belt connector, said expandable intermediate connector and said exterior belt connector, said conduit terminating in the interior of said colostomy bag.

2. A colostomy bag belt comprising:

a skin patch connector having a skin-facing surface, a mating surface and a first aperture extending through said skin patch connector from said skin-facing surface to said mating surface;

a comfort belt having a first inner surface, a first outer surface and a first adjustable closure, said comfort belt having a second aperture therethrough and a tubular inner belt connector disposed in said second aperture;

said skin patch connector being connected in mating fashion to said inner belt connector;

a colostomy bag attached to a conduit formed through said skin patch connector and said inner belt connector, said colostomy bag being attached to said conduit at an end opposite said skin patch;

an exterior belt having a second inner surface, a second outer surface and a second adjustable closure, said exterior belt having a first pouch formed integrally therein, said exterior belt having a tubular exterior belt connector disposed within a third aperture which extends through said second inner surface, said exterior belt further having an opening through said second outer surface which allows access to the interior of said first pouch, said opening being closeable by a zipper which extends along the edges of said opening; and an intermediate connector having a first end and a second end, said first end being connected in mating fashion to said inner belt connector, said second end being connected in mating fashion to said exterior belt connector, said conduit further comprising said intermediate connector and said exterior belt connector.

3. The colostomy bag belt of claim 2, further comprising at least one rubber grip attached to said second inner surface of said exterior belt.

4. The colostomy bag belt of claim 2 further comprising a removable multi-layer pad attached to said first inner surface of said comfort belt.

5. The colostomy bag belt of claim 2 wherein said intermediate connector is expandable and has accordion-style folds which allow said first and second ends to move with respect to each other while maintaining said mating connections.

6. The colostomy bag belt of claim 2 wherein said exterior belt comprises a second, leak-proof pouch disposed within said first pouch, said second, leak-proof pouch having a first wall adjoining said second inner surface and a second wall adjoining said second outer surface, and wherein said third aperture and said tubular exterior belt connector extend through said first wall, and wherein said opening through said second outer surface which allows access to the interior of said first pouch also extends through said second wall of said second pouch.

7. The colostomy bag belt of claim 6 wherein said opening in said second outer surface and said second wall of said second pouch is curved to form a flap which is outwardly extendable from said curved opening and wherein said zipper is leak-proof.

8. The colostomy bag belt of claim 7 wherein said intermediate connector is expandable and has accordion-style folds which allow said first and second ends to move with respect to each other while maintaining said mating connections.

9. The colostomy bag belt of claim 8, further comprising two pleats, one of each of said pleats being disposed on each end of said curved opening to form a reservoir when said flap is outwardly extended.

10. The colostomy bag belt of claim 9, further comprising a removable multi-layer attached to said first inner surface of said comfort belt.

11. The colostomy bag belt of claim 10, further comprising at least one rubber grip attached to said second inner surface of said exterior belt.

12. The colostomy bag belt of claim 10, further comprising:

a plurality mating pairs of snaps, each pair having a male snap and a female snap, one snap of each of said pairs of snaps being attached to said first outer surface of said comfort belt around said comfort belt connector, the other snap of each of said pairs of snaps being attached to said second inner surface of said exterior belt around said exterior belt connector and in alignment with said snaps attached to said comfort belt;

a plurality of pairs of mating hook-and-loop patches, each pair having a patch of hook material and a patch of loop material, one patch of each pair being attached to said first outer surface of said comfort belt around said comfort belt connector, the other patch of each of said pairs of patches being attached to said second inner surface of said exterior belt around said exterior belt connector and in alignment with said patches attached to said comfort belt.

13. The colostomy bag belt of claim 6, further comprising two pleats, one of each of said pleats being disposed on each end of said curved opening to form a reservoir when said flap is outwardly extended.

14. The colostomy bag belt of claim 6, further comprising:

a plurality mating pairs of snaps, each pair having a male snap and a female snap, one snap of each of said pairs of snaps being attached to said first outer surface of said comfort belt around said comfort belt connector, the other snap of each of said pairs of snaps being attached to said second inner surface of said exterior belt around said exterior belt connector and in alignment with said snaps attached to said comfort belt;

a plurality of pairs of mating hook-and-loop patches, each pair having a patch of hook material and a patch of loop material, one patch of each pair being attached to said first outer surface of said comfort belt around said comfort belt connector, the other patch of each of said pairs of patches being attached to said second inner surface of said exterior belt around said exterior belt connector and in alignment with said patches attached to said comfort belt; and wherein said intermediate connector is expandable and has accordion-style folds which allow said first and second ends to move with respect to each other while maintaining said mating connections.

15. The colostomy bag belt of claim 14 wherein said opening in said second outer surface and said second wall of said second pouch is curved to form a flap which is outwardly extendable from said curved opening and wherein said zipper is leak-proof.

16. The colostomy bag belt of claim 15, further comprising two pleats, one of each of said pleats being disposed on each end of said curved opening to form a reservoir when said flap is outwardly extended.

17. The colostomy bag belt of claim 16, further comprising a pocket attached to said second outer surface of said exterior belt.

\* \* \* \* \*